United States Patent
Datla et al.

(10) Patent No.: US 12,398,126 B2
(45) Date of Patent: Aug. 26, 2025

(54) PROCESS TO SYNTHESIZE 5-(3PYRIDYL)-2,2'-BITHIOPHENE (SENSITIZER)

(71) Applicant: FERMENTA BIOTECH LIMITED, Kandivali (East) Mumbai (IN)

(72) Inventors: Anupama Datla, Mumbai (IN); Prashant Nagre, Thane West (IN); Jagdish Tamore, Thane (IN); Sreenath Trivikram, Dombivli (IN); Gajanan Degaonkar, Badlapur (IN)

(73) Assignee: FERMENTA BIOTECH LIMITED, Mumbai (IN)

( * ) Notice: Subject to any disclaimer, the term of this patent is extended or adjusted under 35 U.S.C. 154(b) by 762 days.

(21) Appl. No.: 17/615,757

(22) PCT Filed: Jun. 8, 2020

(86) PCT No.: PCT/IN2020/050506
§ 371 (c)(1),
(2) Date: Dec. 1, 2021

(87) PCT Pub. No.: WO2020/245845
PCT Pub. Date: Dec. 10, 2020

(65) Prior Publication Data
US 2022/0306615 A1    Sep. 29, 2022

(30) Foreign Application Priority Data

Jun. 6, 2019  (IN) .............................. 201921021829

(51) Int. Cl.
*C07D 409/14*  (2006.01)
*B01J 31/02*  (2006.01)

(52) U.S. Cl.
CPC ........ *C07D 409/14* (2013.01); *B01J 31/0244* (2013.01)

(58) Field of Classification Search
CPC ........................... C07D 409/14; B01J 31/0244
USPC ...................................... 546/280.4
See application file for complete search history.

(56) References Cited

U.S. PATENT DOCUMENTS 5,252,191 A * 10/1993 Pauli .................. C07D 409/04
204/157.67

* cited by examiner

*Primary Examiner* — Taylor V Oh
(74) *Attorney, Agent, or Firm* — Kramer & Amado, P.C.

(57) ABSTRACT

The present invention discloses an improved catalytic process for the synthesis of 5-(3-pyridyl)-2,2'-bithiophene in high yield and purity.

17 Claims, No Drawings

PROCESS TO SYNTHESIZE 5-(3PYRIDYL)-2,2'-BITHIOPHENE(SENSITIZER)

FIELD OF INVENTION

The present invention relates to an improved catalytic process for the synthesis of 5-(3-pyridyl)-2,2'-bithiophene (Sensitizer) in high yield.

BACKGROUND OF THE INVENTION

Vitamin D3 i.e. Cholecalciferol, is produced in the human body through the exposure to UVB light on its provitamin 7-dehydrocholesterol (7-DHC).

Vitamin D3 is commercially produced from its isomers such as tachysterol, 7-DHC, cholesterol, phytosterol, ergosterol, lanosterol by subjecting the solution of said sterol/isomers to irradiation at suitable wavelength. However, irradiation processes have certain shortfalls such as it leads to formation of undesirable isomers and requires extensive separation and purification techniques to isolate vitamin D3 which is not industrially feasible as it leads to addition of costs.

With the intended use of vitamin D3, viz. for human or veterinary administration, the final vitamin D3 compound obtained should be produced free from detrimental contaminants. It is therefore essential that the photochemical conversion preferably yields a single well-defined product with the desired properties. Insufficient conversion and/or the formation of by-products during the conversion reaction produce(s) contaminated end product which is often tedious, sometimes even impossible, to purify such reaction products up to a purity suitable for human or veterinary use.

The drawbacks of irradiation processes in in the synthesis of vitamin D3 in the art are overcome by use of photosensitizers such that they block certain wavelengths and aid in resulting the desired end product with minimum or no contamination.

U.S. Pat. No. 5,252,191 discloses substituted thiophene derivatives of general formula (I) having a substantial absorption in the wavelength region of approx. 300-1,000 nm as improved photosensitizer over the art during photochemical conversion of tachysterol compounds into previtamin D compounds and of trans vitamin D compounds into cis-vitamin D compounds.

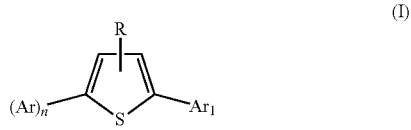

(I)

(variables are as defined in US '191)

One such photosensitizer encompassed in the general Markush structure of Formula (I) in US '191 is 5-(3-pyridyl)-2,2'-bithiophene.

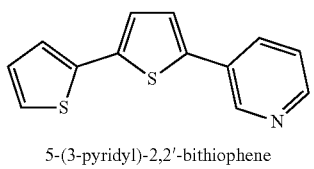 [SMILES: c1cncc(-c2ccc(-c3cccs3)s2)c1]

5-(3-pyridyl)-2,2'-bithiophene

The photosensitizer was observed to block certain undesired wavelengths resulting in good yield and purity of the irradiated/photosynthesis products. Moreover, the said sensitizer can be easily removed from the reaction mixture after the irradiation is complete.

The present inventors while following the general method of preparation of substituted thiophene derivatives of general formula (I) and particularly 5-(3-pyridyl)-2,2' bithiophene disclosed in US '191 worked out the method for preparation of 5-(3-pyridyl)-2,2' bithiophene which comprises reacting 3-dimethylamino-1-(2-thienyl)1-propanone with pyridine-3-carboxaldehyde in presence of sodium cyanide and DME to yield 1-(3-pyridyl)-4-(2-thienyl)-1, 4 butadione which is further reacted with Lawesson reagent to get the final product, 5-(3-pyridyl)-2,2'-bithiophene.

The inventors observed that following the method described in US '191 has certain drawbacks viz. the conversion rate is very low i.e. in the range of 30-40%. Moreover, the process employs sodium cyanide which is a highly hazardous chemical and extra precaution is needed to be taken while storing, handling and disposing the chemical.

In light of the need to employ the photosensitizer, 5-(3-pyridyl)-2,2'-bithiophene, during photochemical conversion to vitamin D compounds the present inventors felt that there remains a scope to synthesize the said photosensitizer in economical and industrially feasible manner over the process disclosed in US '191.

SUMMARY OF THE INVENTION

It is therefore the object of the present invention to provide an improved catalytic method for the preparation of the photosensitizer, 5-(3-pyridyl)-2,2'-bithiophene using safe and easy to handle catalyst i.e. N-Benzyl-4-methyl-5-Hydroxyethyl thiazole hydrochloride.

In accordance with the above, the present invention provides an improved catalytic process for synthesis of 5-(3-Pyridyl)-2,2'-Bithiophene (Sensitizer) in high yield and purity which comprises;
 i. Reacting 2-acetyl Thiophene with paraformaldehyde and Dimethylamine hydrochloride in solvent to give 3-(Dimethylamino)-1-(2-Thienyl)-1-propanone hydrochloride;
 ii. Treating 3-(Dimethylamino)-1-(2-Thienyl)-1-propanone hydrochloride of step (1) with pyridine-3-carboxaldehyde in presence of the catalyst 3-Benzyl-5-(2-Hydroxyethyl)-4-methyl thiazolium hydrochloride, base and solvent to give 1-(2-Thienyl)-4-(3-Pyridyl)-1,4-Butanedione optionally followed by crystallization; and
 iii. Converting 1-(2-Thienyl)-4-(3-Pyridyl)-1,4-Butanedione of step (2) to 5-(3-pyridyl)-2,2'-bithiophene.

DETAILED DESCRIPTION OF THE INVENTION

The invention will now be described in detail in connection with certain preferred and optional embodiments, so that various aspects thereof may be more fully understood and appreciated.

The present invention discloses an improved process for the preparation of the photosensitizer, 5-(3-pyridyl)-2,2'-bithiophene, wherein the improvement is in the use of safe and easy to handle catalyst, N-Benzyl-4-methyl-5-Hydroxyethyl thiazole hydrochloride which results in the formation of the desired product with high conversion rate and in short period of time.

In an embodiment, the present process for preparation of the photosensitizer, 5-(3-pyridyl)-2,2' bithiophene in high yield and purity comprises;

1. reacting 2-Acetyl Thiophene with paraformaldehyde and Dimethylamine hydrochloride in solvent to give 3-(Dimethylamino)-1-(2-Thienyl)-1-propanone hydrochloride;

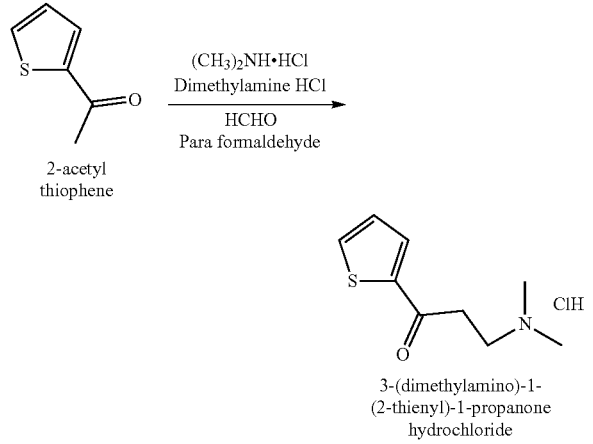

2. treating 3-(Dimethylamino)-1-(2-Thienyl)-1-propanone hydrochloride of step (1) with pyridine-3-carboxaldehyde in presence of the catalyst 3-Benzyl-5-(2-Hydroxyethyl)-4-methyl thiazolium hydrochloride, base and solvent to give 1-(2-Thienyl)-4-(3-Pyridyl)-1,4-Butanedione optionally followed by crystallization;

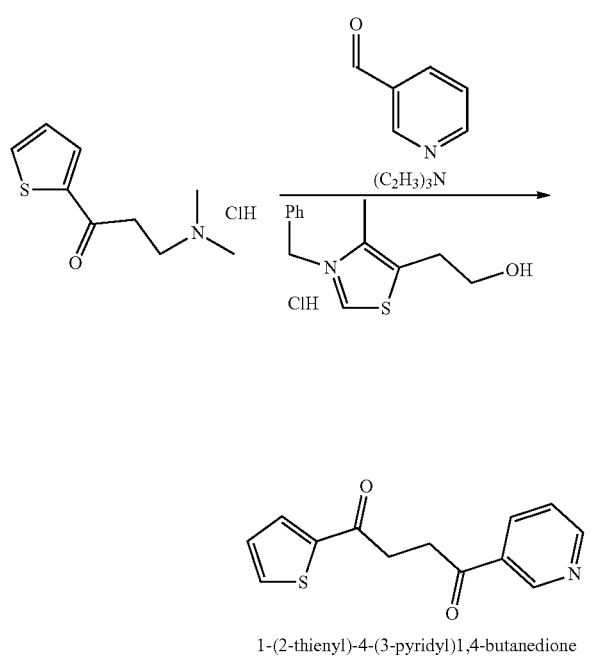

and 3. converting 1-(2-Thienyl)-4-(3-Pyridyl)-1,4-Butanedione to 5-(3-pyridyl)-2,2' bithiophene and optionally purifying.

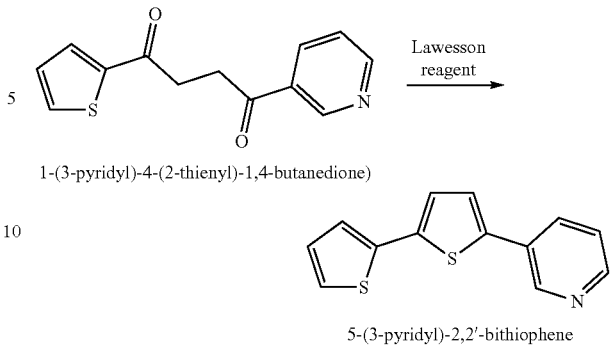

Accordingly, in step (1), 2-Acetyl Thiophene was treated with 1.0 eq-1.6 eq of paraformaldehyde preferably 1-1.4 eq and more preferably 1.1-1.3 equivalents of paraformaldehyde, 1.0-1.7 eq of Dimethylamine hydrochloride preferably 1-1.4 eq & more preferably 1.1-1.3 equivalents of Dimethylamine hydrochloride and 2-20% w/v (with respect to 2-Acetyl thiophene) concentrated Hydrochloric acid preferably 5-8% concentrated hydrochloric acid with 1-6 volumes of solvents selected from alcohols, ethers, ketones and the like alone or mixtures thereof; preferably from C1 to C7 alcohols, more preferably 1.5-3 volumes of Ethanol as a solvent. The reaction mass was heated to 50-120° C. preferably 70-100° C. and more preferably 80-100° C. for 8-40 hours preferably for 16-24 hours. The mass was cooled to −5 to +5° C., the solids were separated out, filtered and further washed with the solvent. The filtered solid was 3-(Dimethylamino)-1-(2-Thienyl)-1-propanone hydrochloride.

In the process step (2) of the present invention, to 3-(Dimethylamino)-1-(2-Thienyl)-1-propanone hydrochloride of step (1) was added 0.2-1.2 equivalents of 3-Benzyl-5-(2-Hydroxyethyl)-4-methyl thiazolium hydrochloride, preferably 0.3 eq-0.9 eq or more preferably 0.35-0.6 eq of 3-Benzyl-5-(2-Hydroxyethyl)-4-methyl thiazolium hydrochloride, 1-2 eq of base suspended in 8-20 volumes of the solvent, preferably 9-15 volumes or more preferably 10-14 volumes. The mixture was heated to 70° C.-140° C. preferably 80-135° C. more preferably 90-100° C. 1-1.5 eq of Pyridine-3-carboxaldehyde preferably 1-1.3 equivalents of Pyridine-3-carboxaldehyde was added drop wise to the heated mixture at 90-100° C. in about 2-6 hours. After complete addition the reaction mass was further heated at 90-100° C. for 12-45 hours, more preferably for 20-30 hours. After 20-30 hours the entire solvent was evaporated under vacuum at 60-85° C. The residue was dissolved in 5-8 volumes of the mixture of hydrocarbon and 5-15 volumes of water. The organic and aqueous layers were separated and the aqueous layer was further extracted with 3*10 volumes of solvent selected from hydrocarbon. The entire organic layer was washed with 2*7-8 volumes of water, dried and evaporated under vacuum. The residue was further crystallized from aq. solvent mixture. Optionally, the residue in the organic layer is used as such without crystallization for subsequent step.

The solvents for the process step (2) of the present invention is selected from polar or non-polar, protic or aprotic solvents such lower alcohols, ethers selected from 1,4 dioxane, methyl tert-butyl ether, THF and the like; aliphatic or aromatic hydrocarbons such as hexane, heptane, toluene, xylene and the like; halogenated hydrocarbons, DMF; esters, ketones and such like alone or mixtures thereof.

The base for the reaction is selected from ethylamine, triethylamine, pyridine and the like.

In an embodiment, the process step 2 of the present invention employs safe and easy to handle catalyst that results in higher conversion rate in the range of 75-80%. The catalyst, 3-Benzyl-5-(2-Hydroxyethyl)-4-methyl thiazolium hydrochloride used in process step (2) can easily be separated during the crystallization in second or third step and can safely be used on a larger scale.

The Step (3) of the process comprises reacting crude 1-(2-Thienyl)-4-(3-Pyridyl)-1,4-Butanodione of stop (2) dissolved in 5-50 volumes of solvent which include but is not limited to aliphatic or aromatic hydrocarbons, ethers, ketones, halogenated hydrocarbons; preferably 6-volumes, more preferably 6-12 volumes with 0.51 eq of 2,4-Bis(4-methoxyphenyl)-1,3-Dithia-2,4-Diphosphetane-2,4-disulfide. The reaction mass was heated at 60-145° C. preferably at 70-140° C. more preferably at 85-140° C. for 2-10 hours preferably for 3-8 hours, more preferably at 4-6 hours until TLC indicated completion of the reaction. The reaction mass was cooled to 28-30° C. IN-10N Sodium hydroxide was added till the pH was 10. The organic and the aqueous layers were separated. The aqueous layer was extracted with 2*5 volumes of solvent. The entire organic layer was washed with 3*1 volume of water, dried evaporated under vacuum to obtain crude product 5-(3-Pyridyl)-2,2'-Bithiophene.

The crude 5-(3-Pyridyl)-2,2'-Bithiophene obtained by the process of the present invention is further purified/crystallized from the solvents selected from polar or non-polar, protic or aprotic solvent such as water, nitriles, C1-C6 alcohols, aliphatic or aromatic hydrocarbons, ketones, ethers, esters and like alone or mixtures thereof. The crude product may also be purified by column chromatography using silica gel and eluents selected from polar or non-polar, protic or aprotic solvent.

Accordingly, the crude product was purified/crystallized in one of the following ways:

(1). The crude product (1 equivalent) was dissolved in 3-10 volumes of Acetonitrile preferably 4-9, more preferably 4-8 volumes of acetonitrile, heated to 80-85° C. for about 30 minutes, cooled gradually at the rate of 10° C./hour to 0° C., stirred at 0° C. for about 3 hours. The solid separated out were filtered, washed with cold acetonitrile, and dried under vacuum.

(2). The crude product may also be purified over silica gel with Toluene:Methanol (95:5, 90:10, 85:15, 80:20) or Ethyl acetate:Methanol (98:2, 95:5, 90:10) or Dichloromethane:Methanol (95:5, 90:10) as eluent.

(3). The crude product was dissolved in 2.5-5 volumes of Toluene preferably 2.5-3 volumes of Toluene heated to 95-98° C. 5-10 volumes of n-hexane preferably 5-6 volumes of n-heptane or n-hexane was added and cooled to 10-40° C. The upper layer was decanted and cooled to −10-+30° C. preferably-5 to 10° C. or more preferably to 0-10° C., stirred at 0-10° C. for about 3 hours. The solids were filtered and washed with 2 volumes of n-heptane or n-hexane, dried under vacuum.

In an embodiment, the present invention provides economical and industrially feasible process for synthesis of the photosensitizer, 5-(3-Pyridyl)-2,2'-Bithiophene, useful in the irradiation processes for production of vitamin D3 with reduced contamination.

The invention will now be described in the following specific examples, however, it is being understood that the particulars shown are solely for purpose of illustrative discussion of preferred embodiments of the invention.

Reference Example 1: Preparation of 1-(2-Thienyl)-4-(3-Pyridyl)-1,4-Butanedione (as Per US '191)

3-Dimethylamino-1-(2-Thienyl)-1-propanone was treated with sodium cyanide in dry dimethylformamide at 25-30° C. 3-Pyridine carboxaldehyde in dimethylformamide was added and the resulting reaction mass was stirred at 25-30° C. for 60 hours. After work up 1-(3-Pyridyl)-4-(2-Thienyl)-1,4-butadione was isolated.

Yield: 24%

Example 1: Preparation of 3-(Dimethylamino)-1-(2-Thienyl)-1-propanone hydrochloride 200 gms (1.58M, 1 eq) of 2-Acetylthiophene was dissolved in 100 ml Ethanol. 58 gms (1.933M, 1.22 eq) of para formaldehyde, 160 gms (1.963M, 1.24M) of Dimethyl amine hydrochloride, 16 ml (8%) of Concentrated Hydrochloric acid and 200 ml of Ethanol were added. The entire reaction mass was refluxed (80-85° C.) for 24-28 hours. After 28 hours the reaction mass was cooled to 0-5° C. The solid was separated out, filtered, washed with 500 ml of Ethanol. The wet product was dried at 80-85° C. for 16-24 hours.

Yield: 310 gms
% Yield: 89%

Example 2: Synthesis of 1-(2-Thienyl)-4-(3-Pyridyl)-1,4-Butanedione 300 gms (1.36M, 1 eq) of 3-(Dimethylamino)-1-(2-Thienyl)-1-propanone hydrochloride of example 1, 160 gms (0.5930M, 0.43 eq) of 3-Benzyl-5-(2-Hydroxyethyl)-4-methyl thiazolium hydrochloride and 138 gms (1.36 M, 1 eq) of Triethyl amine were suspended in 3600 ml of dry 1,4-Dioxane. The suspension was heated to 90-95° C. 180 gms (1.68M, 1.23 eq) of Pyridine-3-carboxaldehyde was added at 90-95° C. in a duration of 30 minutes. The reaction was heated at 90-100° C. for 22 hours. TLC and Gas chromatographic analysis indicates 70-82% conversion. The reaction was stopped and the entire solvent was evaporated under vacuum at 50-80° C. The residue was suspended in 2 litres of Toluene, filtered and the filtrate was washed with 3 liters of water. The aqueous layer was re-extracted with 3*3 liters of Toluene. The entire Toluene layer was washed with 2*2 liters water, dried over anhydrous sodium sulphate and used as such in Step 3.

GC purity 75-80%
Crystallization:
500 ml of Toluene layer containing the solid was evaporated under vacuum at 40-50° C. 150 ml of water is added to the residual oil and stirred for 30 minutes at 28-30° C. The water was decanted and again treated with 150 ml water, stirred for 1 hour, solids were separated, filtered, washed with 50 ml of 1:1 Ethanol:water. After stirring with 100 ml of 4:1 Ethanol:Water mixture the solids were dried under vacuum at 40-50° C. for 3 hours.

Yield: 15 gms
GC purity: 92-94%

Example 3: Preparation of 5-(3-Pyridyl)-2,2'-Bithiophene (Sensitizer/Photosensitizer)

To 300 gms (1.22M, 1 eq) of crude 1-(2-Thienyl)-4-(3-Pyridyl)-1,4-Butanedione of example 2 in 2 liters of Toluene 252 gms (0.623M, 0.51 eq) of 2,4-Bis(4-methoxyphenyl)-1,3-Dithia-2,4-Diphosphetane-2,4-disulfide was added and the reaction mass was refluxed for 4-5 hours until TLC and GC analysis indicated completion of reaction and formation of the desired product. The reaction mass was cooled to 28-30° C., 5N Sodium Hydroxide was added to the reaction mass till pH was 10-11, stirred for 30 minutes at 40-50° C. The organic and the aqueous layers were separated and the aqueous layers was extracted with 2*1.5 liters of Toluene. The entire Toluene layer was washed with 3*300 ml of water, dried over anhydrous sodium sulphate and the solvent was evaporated under vacuum at 40-50° C. The residue of 325 gms was dissolved in 2600 ml of Acetonitrile and heated to 80-85° C. for 1 hour. After 1 hour the clear solution was cooled gradually at the rate of 10° C./hour to 0-10° C. The solids separated were filtered, washed with 650 ml of chilled Acetonitrile, dried under vacuum at 40-50° C.

Yield: 190 gms
GC purity: 99.45%

The mother liquor was evaporated and the residue (120 gms) was dissolved in 1 liter of Acetonitrile, heated to 80-85° C. for 1 hour. After 1 hour the clear solution was cooled gradually at the rate of 10° C./hour to 0-10° C. The solids separated were filtered, washed with 240 ml of chilled Acetonitrile, dried under vacuum at 40-50° C.

Yield: 32 gms
GC purity: 99.15%
Melting point: 86-87° C.

Example 4: Purification/Crystallization of 5-(3-Pyridyl)-2,2'-Bithiophene

4a: The crude product (10 gms) is dissolved in 70 ml of Acetonitrile, heated to 80-85° C. for 30 minutes, cooled gradually at the rate of 10° C./hour to 0° C., stirred at 0° C. for 3 hours. The solid separated out are filtered, washed with 30 ml of cold acetonitrile, and dried under vacuum at 40-50° C. for 2 hours.

Yield: 7 gms equivalents
GC purity: 98.5%-99.7%

4b: The crude product (10 gms) can also be purified over silica gel (60-200 mesh) with Toluene:Methanol (100:0, 95:5, 90:10, 85:15, 80:20)

Yield: 7.3 gms
GC purity: 99-99.5%

4c: The crude product (10 gms) was dissolved in 30 ml of Toluene, heated to 95-98° C. 60 ml of n-hexane and cooled to 10-40° C. The upper layer is decanted and cooled to −10-+30° C. preferably −5 to 10° C. or more preferably to 0-10° C., stirred at 0-10° C. for 3 hours. The solids are filtered and washed with 20 ml volumes of n-hexane, dried under vacuum at 40-50° C.

Yield: 6.5 gms
GC purity: 97-99.5%

This method is a bit tedious as the desired compound is more soluble in Toluene and hence the desired compound was lost in the mother liquor. The mother liquor was further evaporated under vacuum and the residue was again similarly purified.

We claim:
1. A catalytic process for synthesis of 5-(3-pyridyl)-2,2'-bithiophene, comprising:
   i. reacting 2-acetylthiophene with paraformaldehyde and dimethylamine hydrochloride in a first solvent to give 3-(dimethylamino)-1-(2-thienyl)-1-propanone hydrochloride;
   ii. treating the 3-(dimethylamino)-1-(2-thienyl)-1-propanone hydrochloride with pyridine-3-carboxaldehyde in the presence of a catalyst, a base and a second solvent to give 1-(2-thienyl)-4-(3-pyridyl)-1,4-butanedione, wherein the catalyst is 3-benzyl-5-(2-hydroxyethyl)-4-methyl thiazolium hydrochloride; and
   iii. reacting the 1-(2-thienyl)-4-(3-pyridyl)-1,4-butanedione with 2,4-bis(4-methoxyphenyl)-1,3-dithia-2,4-diphosphetane-2,4-disulfide to produce 5-(3-pyridyl)-2,2'-bithiophene;
   wherein the second solvent is the same as or different from the first solvent.

2. The catalytic process as claimed in claim 1, wherein; the first solvent is selected from the group consisting of an alcohol, an ether, a ketone, and mixtures thereof, and the second solvent is selected from the group consisting of polar solvents, non-polar solvents, protic solvents, aprotic solvents, and mixtures thereof.

3. The catalytic process as claimed in claim 1, wherein the base is selected from the group consisting of ethylamine, triethylamine, pyridine, and mixtures thereof.

4. The catalytic process as claimed in claim 1, wherein the step of reacting 2-acetyl thiophene with paraformaldehyde and dimethylamine hydrochloride is carried out at a temperature in the range of 50-120° C.

5. The catalytic process as claimed in claim 1, wherein the step of treating the 3-(dimethylamino)-1-(2-thienyl)-1-propanone hydrochloride with pyridine-3-carboxaldehyde is carried out at a temperature in the range of 70° C.-140° C.

6. The catalytic process as claimed in claim 5, wherein the step of treating the 3-(dimethylamino)-1-(2-thienyl)-1-propanone hydrochloride with pyridine-3-carboxaldehyde is carried out for 12-45 hours.

7. The catalytic process as claimed in claim 1, wherein the second solvent is selected from the group consisting of lower alcohols, ethers, ketones, esters, hydrocarbons, halogenated hydrocarbons, and mixtures thereof.

8. The catalytic process as claimed in claim 4, wherein the step of reacting 2-acetyl thiophene with paraformaldehyde and dimethylamine hydrochloride is carried out at a temperature in the range of 70-100° C.

9. The catalytic process as claimed in claim 8, wherein the step of reacting 2-acetyl thiophene with paraformaldehyde and dimethylamine hydrochloride is carried out at a temperature in the range of 80-100° C.

10. The improved catalytic process as claimed in claim 5, wherein the step of treating the 3-(dimethylamino)-1-(2-thienyl)-1-propanone hydrochloride with pyridine-3-carboxaldehyde is carried out at a temperature in the range of 80° C.-135° C.

11. The improved catalytic process as claimed in claim 10, wherein the step of treating the 3-(dimethylamino)-1-(2-thienyl)-1-propanone hydrochloride with pyridine-3-carboxaldehyde is carried out at a temperature in the range of 90° C.-100° C.

12. The catalytic process as claimed in claim 6, wherein the step of treating the 3-(dimethylamino)-1-(2-thienyl)-1-propanone hydrochloride with pyridine-3-carboxaldehyde is carried out for 20-30 hours.

13. The catalytic process as claimed in claim 1, further comprising a step of crystallizing the 5-(3-pyridyl)-2,2'-bithiophene from a crystallization solvent selected from the group consisting of polar solvents, non-polar solvents, protic solvents, aprotic solvents, and mixtures thereof.

14. The catalytic process as claimed in claim 1, further comprising a step of crystallizing the 5-(3-pyridyl)-2,2'-bithiophene from a crystallization solvent selected from the group consisting of water, nitriles, C1-C6 alcohols, aliphatic or aromatic hydrocarbons, ketones, ethers, esters, and mixtures thereof.

15. A catalytic process for synthesis of 1-(2-thienyl)-4-(3-pyridyl)-1,4-butanedione, comprising;
   i. reacting 2-acetylthiophene with paraformaldehyde and dimethylamine hydrochloride in a first solvent to give 3-(dimethylamino)-1-(2-thienyl)-1-propanone hydrochloride; and
   ii. treating the 3-(dimethylamino)-1-(2-thienyl)-1-propanone hydrochloride with pyridine-3-carboxaldehyde in the presence of a catalyst, a base and a second solvent to give 1-(2-thienyl)-4-(3-pyridyl)-1,4-butanedione, wherein the catalyst is 3-benzyl-5-(2-hydroxyethyl)-4-methyl thiazolium hydrochloride.

16. A process for synthesis of 5-(3-pyridyl)-2,2'-bithiophene, comprising:
   synthesizing 1-(2-thienyl)-4-(3-pyridyl)-1,4-butanedione by the process of claim 15, and
   reacting the 1-(2-thienyl)-4-(3-pyridyl)-1,4-butanedione with 2,4-bis(4-methoxyphenyl)-1,3-dithia-2,4-diphosphetane-2,4-disulfide at a temperature of 60° C. to 145° C. to produce 5-(3-pyridyl)-2,2'-bithiophene.

17. The catalytic process as claimed in claim 15, wherein:
   the first solvent is selected from the group consisting of an alcohol, an ether, a ketone, and mixtures thereof, and
   the second solvent is selected from the group consisting of lower alcohols, ethers, ketones, esters, hydrocarbons, halogenated hydrocarbons, and mixtures thereof.

* * * * *